US009259206B2

(12) United States Patent
Degertekin et al.

(10) Patent No.: US 9,259,206 B2
(45) Date of Patent: Feb. 16, 2016

(54) CMUT-ON-CMOS BASED GUIDEWIRE INTRAVASCULAR IMAGING

(71) Applicant: Georgia Tech Research Corporation, Atlanta, GA (US)

(72) Inventors: F. Levent Degertekin, Atlanta, GA (US); Maysam Ghovanloo, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 123 days.

(21) Appl. No.: 14/185,728

(22) Filed: Feb. 20, 2014

(65) Prior Publication Data

US 2014/0236017 A1    Aug. 21, 2014

Related U.S. Application Data

(60) Provisional application No. 61/766,719, filed on Feb. 20, 2013, provisional application No. 61/857,883, filed on Jul. 24, 2013.

(51) Int. Cl.
*A61B 8/12* (2006.01)
*A61B 8/00* (2006.01)
*B06B 1/02* (2006.01)

(52) U.S. Cl.
CPC . *A61B 8/12* (2013.01); *A61B 8/445* (2013.01); *A61B 8/56* (2013.01); *B06B 1/02* (2013.01); *B06B 1/0292* (2013.01); *A61B 8/4444* (2013.01); *A61B 8/4488* (2013.01); *B06B 2201/76* (2013.01)

(58) Field of Classification Search
CPC ........ A61B 8/12; A61B 8/4444; A61B 8/445; A61B 8/4488; A61B 8/56
See application file for complete search history.

(56) References Cited

U.S. PATENT DOCUMENTS

| 7,332,850 | B2 * | 2/2008 | Ladabaum et al. | 310/334 |
|---|---|---|---|---|
| 2005/0121734 | A1 * | 6/2005 | Degertekin et al. | 257/414 |
| 2005/0124884 | A1 * | 6/2005 | Bolorforosh et al. | 600/439 |
| 2005/0146247 | A1 * | 7/2005 | Fisher et al. | 310/334 |
| 2010/0168583 | A1 * | 7/2010 | Dausch et al. | 600/466 |
| 2012/0091371 | A1 * | 4/2012 | Vartanian et al. | 250/505.1 |
| 2014/0005521 | A1 * | 1/2014 | Kohler et al. | 600/411 |
| 2014/0307528 | A1 * | 10/2014 | Dekker et al. | 367/178 |
| 2014/0336485 | A1 * | 11/2014 | Mujeeb-U-Rahman et al. | 600/345 |

* cited by examiner

*Primary Examiner* — Baisakhi Roy
(74) *Attorney, Agent, or Firm* — Troutman Sanders LLP; Ryan A. Schneider; Mark Lehi Jones

(57) ABSTRACT

An intravascular guidewire with integrated imaging and pressure measurement capabilities is disclosed. The guidewire can comprise an integrated CMUT-on-CMOS ultrasound transducer array to provide 3D imaging of vasculature and other tissue. The guidewire can also comprise a conventional FFR pressure sensor or Doppler flow sensor. Due to the low power consumption of the chip, power can be provided via a single pair of wire pair proximate the core wire of the guidewire to provide power and ground to the chip. The system can also include a power wire, a ground wire, and a data wire, the data wire using similar data transmission techniques. Data from the sensor array can be transmitted over the power wire using, for example, RF or impedance modulation. Data can also be transmitted through the body using an ultra wideband wireless transmitter and flexible patch antenna on the skin.

22 Claims, 13 Drawing Sheets

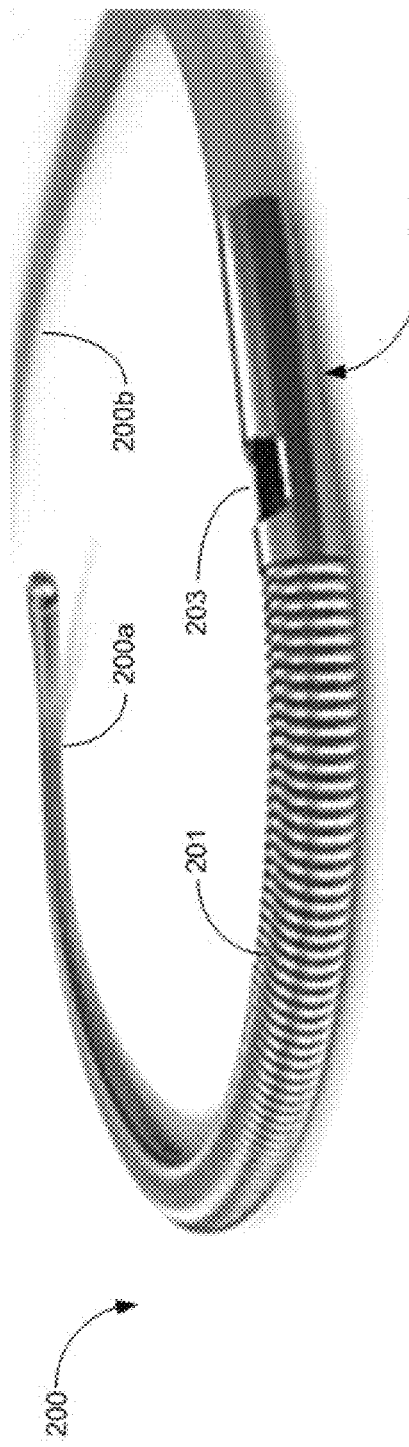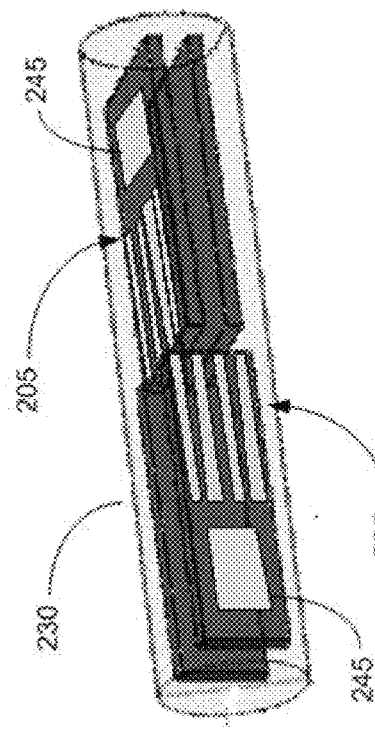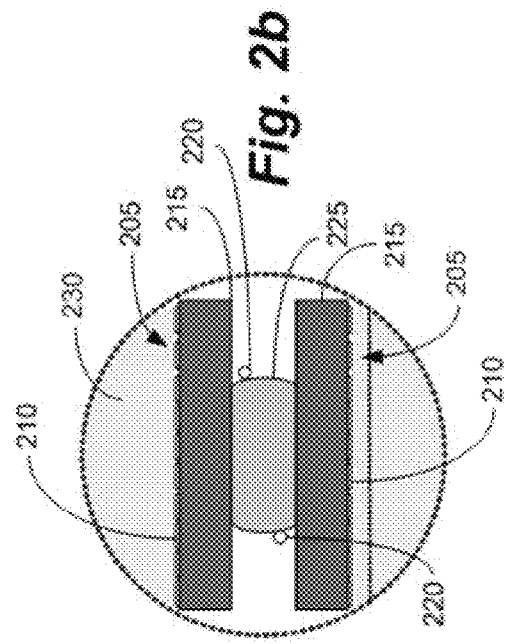

CMUT-ON-CMOS BASED GUIDEWIRE INTRAVASCULAR IMAGING

CROSS-REFERENCE TO RELATED APPLICATIONS AND PRIORITY CLAIM

This application claims priority under 35 U.S.C. §119(e) to, and the benefit of, U.S. Provisional Patent Application No. 61/766,719, entitled "Miniature IVUS Imaging Systems with Wireless Data Readout," filed Feb. 20, 2013, and U.S. Provisional Patent Application No. 61/857,883, of the same title, and filed Jul. 24, 2013, both of which are hereby incorporated by reference as if set forth below in their entirety.

BACKGROUND OF THE INVENTION

1. Field of the Invention

Embodiments of the present invention relate to ultrasound imaging probes, and particularly, to flexible, capacitive micromachined ultrasonic transducer (CMUT) based guidewire ultrasound imaging probes using CMUT arrays integrated with Complementary metal-oxide-semiconductor (CMOS) electronics, and integration of pressure (e.g. fractional flow reserve (FFR)) sensors with the same imaging probe.

2. Background of Related Art

Side-looking intravascular ultrasound ("IVUS") imaging probes exist that provide relatively high resolution images of tissue and fluid. This can be useful, for example, when inspecting the inside surfaces of vessels or tissues immediately surrounding the vessel.

In order to navigate tortuous arteries and coronary structures, for example, an important aspect of IVUS probes is the size and flexibility of the probes. As a result, the rigid section of the probe close to the imaging tip should be as short as small in diameter as possible. Current ultrasound array probes used for these purposes are rigid over several mm, limiting their maneuverability.

During cardiac or other vascular procedures, the surgeon first inserts a guidewire in to the desired artery, sometimes anchoring it in place. The surgeon then uses a series of catheters that are "threaded" over the guidewire. In order to change catheters, e.g., from a balloon catheter to an imaging catheter, the first catheter must be completely removed and the second catheter inserted. This must be done carefully to avoid injuring the vessels walls and thus, can take a significant amount of time—generally 15-20 minutes. Both the extra time involved and the increased risk of incidental injury increase the risks associated with the procedure. As a result, while IVUS greatly improves the outcome of intravascular procedures, for example, it is only used in approximately 20% of intravascular procedures.

In contrast, guidewires are used in nearly 100% of intravascular procedures. Thus, an imaging array integrated into a standard guidewire would eliminate the need to change catheters during the procedure. The surgeon could simply image the vessel as the guidewire is being inserted, during the interventional procedure or after the procedure without a need to exchange catheters. This would improve the outcome of intravascular procedures with no increase in the time or risks associated with removing and inserting multiple catheters.

To maintain the flexibility and mechanical properties of the guidewire, however, the number of electrical connections connecting the probe electronics to the back end imaging system should be limited. In other words, a larger number of cables would make the guidewire thicker and less flexible. The number of external connections is also important, for example, because it adversely affects the mechanical performance of the guidewire if the core of the guidewire is thinned down to make space for the electrical connection wires without increasing the diameter of the guidewire.

In addition to size constraints, ultrasound probes typically must limit their power consumption. When the probe is activated, the temperature of the probe must be limited to prevent damage to surrounding tissue, or simply to prevent the probe from overheating when in open air. In some instances, for example, the probe may remain active outside the body. In this instance, power consumption should be limited to prevent the probe electronics from overheating and damaging the mechanical structure of the probe such as the adhesion layers or coatings.

Measurement of pressure in the blood vessels to obtain FFR information has proven to be useful in evaluating the treatment options in cardiovascular interventions. Therefore, integrating this functionality to the IVUS imaging guidewire is desirable because it enables the use of a single guidewire to better evaluate the condition of the blood vessels.

What is needed, therefore, is a CMUT-CMOS integrated ultrasonic probe on a standard guidewire-sized package. The probe should include reduced power consumption through custom electronics design and intelligent power management. The probe should comprise improved resolution with minimal cross-sectional area and interconnects along the catheter. The probe may also include an integrated FFR sensor to or Doppler sensor to measure blood pressure and/or flow while providing ultrasound imaging. It is to such an ultrasonic probe that embodiments of the present invention are primarily directed.

SUMMARY OF THE INVENTION

Embodiments of the present invention relate to a guidewire for use in intravenous procedures comprising integrated imaging and/or pressure sensing. In some embodiments, the guidewire can comprise one or more capacitive micromachined ultrasonic transducer (CMUT) sensor arrays on a complementary metal-oxide-semiconductor (CMOS) chip, which are either monolithically integrated or in a stacked, multi-chip configuration. The CMUT on CMOS architecture can enable miniaturization of a CMUT array small enough to implement an imaging device on a guidewire with a diameter as small as ~0.014" (i.e., the approximate size of current standard guidewires used in coronary arteries).

In some embodiments, the CMUT arrays can be configured in multiple orientations to enable imaging approximately 360° of tissue around the guidewire. Data can be retrieved from the system in a number of ways including, but not limited to, wirelessly using ultra-wideband wireless technology. In other embodiments, data can also be retrieved using only two wires. In this configuration, a first wire can carry both a differential (symmetrical) AC power signal and an RF signal (or other carrier signal). In another configuration one wire can carry the AC power and RF signal and a second, ground wire. Moreover, the data can be relayed back from the electronics at the distal end of the catheter using back telemetry or load-shift keying (LS K). In still other embodiments, data can be transmitted using three or four wires: two wires for AC power, and ground, a third wire for an RF signal (or other carrier signal), and fourth wire, if needed, carrying a shared, or separate, ground.

Embodiments of the present invention can comprise a system for use with intravascular guidewires comprising a capsule comprising one or more CMUT imaging arrays disposed on a first silicon chip, one or more CMOS electronic devices disposed on the first silicon chip and electrically connected to the one or more CMUT imaging arrays, and an acoustically transparent material encasing the first silicon chip. In some embodiments, the one or more CMOS electronic devices can be disposed on a second silicon chip and the second silicon chip can be electrically connected to the first silicon chip. In other embodiments, the first silicon chip can further comprise one or more fractional flow reserve (FFR) sensors. In still other embodiments, the first silicon chip can further comprise one or more flow sensors.

In some embodiments, the system can comprise a first wire providing a ground to the first silicon chip and a second wire providing power to, and communications from, the first silicon chip. In some embodiments, the second wire can provide communications from the first silicon chip using, for example, back telemetry or load-shift keying (LSK). In still other embodiments, the first wire can provide a ground to the first silicon chip, the second wire can provide AC power to the first silicon chip, and a third wire can carry RF communications from the first silicon chip.

In some embodiments, the system can comprise a first CMUT imaging array disposed on a first side of a first silicon chip, a second CMUT imaging array disposed on a first side of a second silicon chip, a third CMUT imaging array disposed on a first side of a third silicon chip, and a fourth CMUT imaging array disposed on a first side of a fourth silicon chip. In this configuration, the first side of the first silicon chip can be disposed approximately 180° from the first side of the second silicon chip, the first side of the first silicon chip can be disposed approximately 90° from the first side of the third silicon chip, and the first side of the third silicon chip can be disposed approximately 180° from the first side of the fourth silicon chip. In some embodiments, the diameter of the capsule can be less than approximately 0.014".

Embodiments of the present invention can also comprise a system for intravascular imaging comprising a guidewire with a first diameter and comprising a proximal end, a distal end, and a core wire. The system can also comprise a first electronics compartment, with a second diameter, which can be disposed proximate the distal end of the guidewire and can comprise a window. In some embodiments, the system can further comprise one or more CMUT imaging arrays disposed on a first silicon chip and one or more CMOS electronic devices disposed on the first silicon chip and electrically connected to the one or more CMUT imaging arrays. In some embodiments, the first silicon chip can be disposed in the electronics compartment.

In some embodiments, the first diameter and the second diameter can be less than or equal to approximately 0.014". In some embodiments, the one or more CMOS electronic devices can be disposed on a second silicon chip and the second silicon chip can be electrically connected to the first silicon chip. In other embodiments, the system can further comprise one or more flow sensors disposed on one or more of the first silicon chip and the second silicon chip. In some embodiments, the system can comprise one or more fractional flow reserve (FFR) sensors disposed on one or more of the first silicon chip and the second silicon chip. In other embodiments, the system can further comprise an acoustically transparent material encasing the first silicon chip to conform to the internal dimensions of the electronics compartment.

Embodiments of the present invention can also comprise a system comprising a wireless transmitter disposed on the first silicon chip for transmitting data and an external antenna for receiving the data. In some embodiments, the wireless transmitter can comprise an ultra-wideband (UWB) wireless transmitter. In other embodiments, the external antenna can comprises a high-gain patch antenna disposed in close proximity to the wireless transmitter. In some embodiments, the one or more CMUT imaging arrays can comprise one-dimensional (1D) or one and a half dimensional (1.5D) imaging arrays.

Embodiments of the present invention can also comprise a system for intravascular imaging comprising a guidewire with a first diameter and comprising a proximal end, a distal end, and a core wire. In some embodiments, the system can also comprise a plurality of electronics compartments, each with a second diameter, disposed proximate the distal end of the guidewire each comprising a window. The system can also comprise a plurality of CMUT imaging arrays disposed on a plurality of silicon chips and a plurality of CMOS electronic devices disposed on the plurality of silicon chips and electrically connected to the plurality of CMUT imaging arrays. In some embodiments, at least one of the plurality of CMUT imaging arrays and at least one of the plurality of CMOS electronic devices can be disposed in each of the plurality of electronics compartments.

These and other objects, features and advantages of the present invention will become more apparent upon reading the following specification in conjunction with the accompanying drawing figures.

BRIEF DESCRIPTION OF THE FIGURES

FIG. 2a depicts a guidewire with integrated intravascular ultrasound (IVUS), in accordance with some embodiments of the present invention.

FIG. 2b depicts a cross-sectional view of the guidewire with integrated IVUS of FIG. 2a, in accordance with some embodiments of the present invention.

FIG. 2c depicts a perspective, side view of the IVUS sensor capsule, in accordance with some embodiments of the present invention.

DETAILED DESCRIPTION

Figure 1:
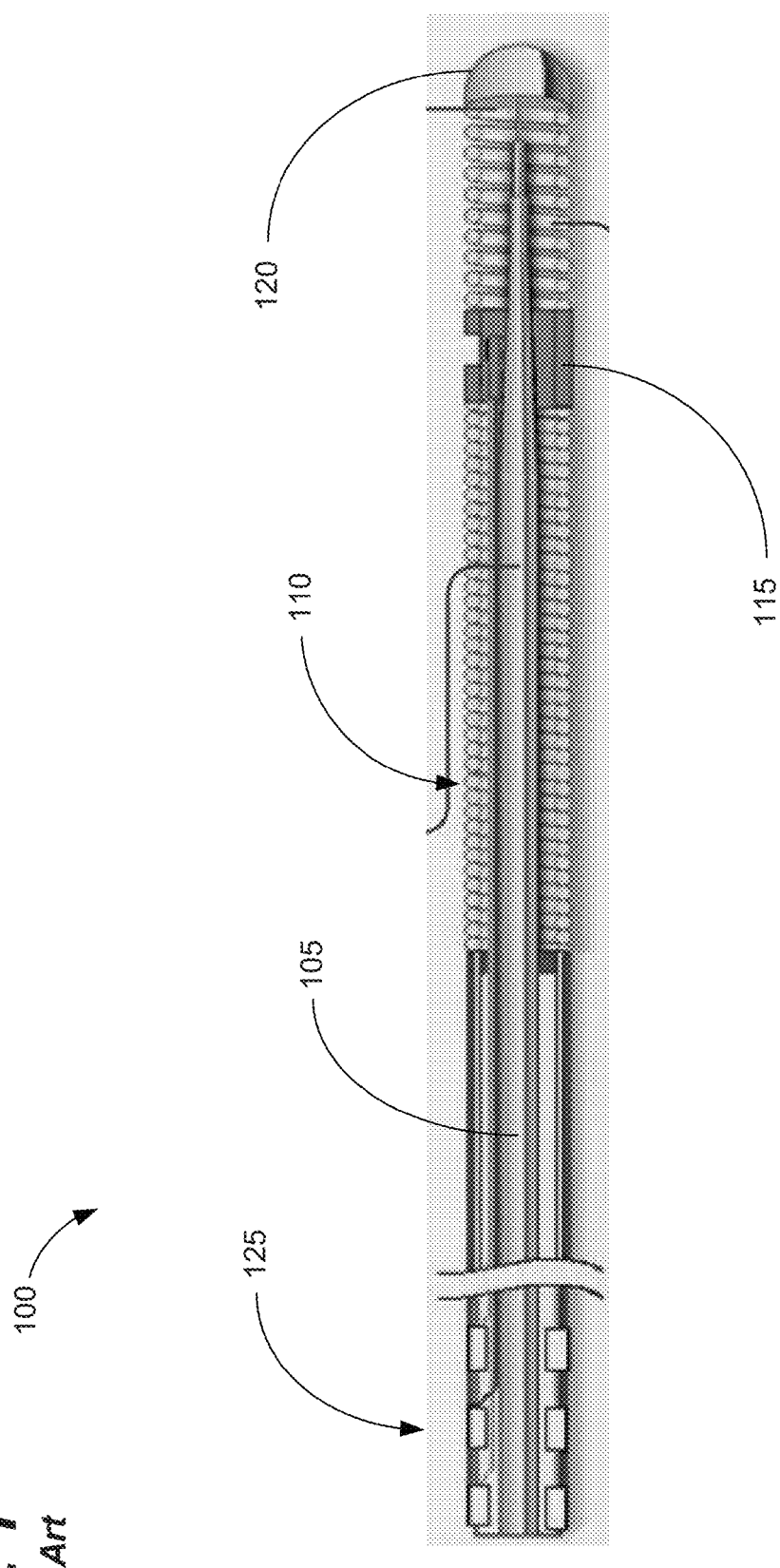
FIG. 1 depicts a schematic cross section of a prior art 0.014" PrimeWire Prestige pressure guide wire by Volcano Corporation.

Embodiments of the present invention relate to an ultrasound imaging probe with substantially reduced size, optimized electronics, intelligent power management, physical imaging array configurations, wireless ultra wideband data transmission antenna, and improved architecture for data readout with minimum number of physical electrical connections running through the catheter. Embodiments of the present invention provide full cross sectional ultrasound images of blood vessels in a very small form factor, transmission of RF image data and AC power using only a few wires and local blood pressure and/or flow information with the same imaging probe. This can be achieved using a multifaceted approach including, but not limited to, careful selection of probe electronics, intelligent power and data management, ultra wideband data telemetry, improved capacitive micromachined ultrasonic transducer (CMUT) on complementary metal-oxide-semiconductor (CMOS) architecture, and unique geometrical arrangements of CMUT arrays. CMUT on CMOS architecture can enable the integration of a high resolution intravascular ultrasound probe integrated into a standard intravascular guidewire.

To simplify and clarify explanation, the system is described below as a system for intravascular ultrasound imaging. One skilled in the art will recognize, however, that the invention is not so limited. The system can also be deployed for other ultrasound imaging applications, particularly when a small catheter cross-section is desired to reach through small openings, for example. The system can also comprise an energy efficient, miniaturized chip for ultrasound imaging.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As mentioned above, a problem with current intravascular ultrasound (IVUS) imaging systems is that, as with other tools used in intravascular procedures (e.g., balloon catheters), they are incorporated into catheters. As a result, in order to be utilized, the catheter must be inserted over the guidewire to obtain imaging. After imaging, the imaging catheter must be removed and a catheter containing another tool must be inserted. The insertion and removal of catheters takes significant time (on the order of 15-20 min.), which affects the outcome of any surgical procedure. In addition, it is possible for the catheters to snag vessel walls and other tissue causing injury and/or bleeding. As a result, imaging is used in a very small number of procedures despite the fact that imaging significantly improves the outcomes of intravascular, and other, procedures.

Guidewires 100, on the other hand, are used in nearly 100% of intravascular procedures. Guidewires 100 are small (~0.014"), flexible wires with specific mechanical properties. As shown in FIG. 1, guidewires generally comprise a central, or core, wire 105 with a flexible, coiled distal end 110. The coiled end 110 enables the wire 100 to be rotated and manipulated to a certain extent to enable, for example, turning through a tortuous artery. The wires 100 generally also have a soft, rounded tip 120 on the distal end to minimize damage to surrounding tissues.

Conventional guidewires 100 do sometimes contain minimal electronics and sensors. As in FIG. 1, over the past decade guidewire based measurements such as fractional flow reserve (FFR) using pressure sensors 115, for example, have proved clinically relevant for intermediate lesion assessment. As shown in FIG. 1, these 0.014" guidewires (such as, for example and not limitation, Volcano PrimeWire Prestige or St. Jude Medical PressureWire Aeris) can include a pressure sensor close 115 to the tip 120 for FFR. These systems typically provide electrical signals through 3 wires wrapped around the solid core 105 and electrical connections 125 located at the proximal end of the wire (i.e., the portion of the wire that is outside the body in use). Manufacturing advances have also made it possible to integrate a Doppler sensor for flow measurement in addition to FFR with 5 electrical wires on the guidewire 100.

In contrast, conventional IVUS imaging guidewire concepts have not been successful, at least in part, because the proposed rotating single element or optical-acoustic systems are too complex to implement within the dimensions of the guidewire without altering its mechanical characteristics. In other words, the large number of cables and interconnects for these systems has, thus far, undesirably increased the stiffness of the guidewire. Similarly, other types of IVUS probes such as, for example, piezoelectric phased array based IVUS systems are not currently viable because of the large size of the minimum feasible piezoelectric array, complexity of the array-electronics interconnects, and the large number of electrical cables required.

As a result, embodiments of the present invention relate to an innovative approach based on recent developments in CMUT-on-CMOS integration along with improved data transmission schemes such as, for example, ultra-wideband wireless, RF-over-power, or back telemetry data communication. This development improves vascular intervention outcomes by providing guidewires with the FFR-IVUS combination, a combination which can have significant clinical value for accurately predicting hemodynamically significant lesions in coronary and peripheral arteries. In addition, the resulting "3-in-1" device can reduce procedure time and cost and reduce equipment costs.

An IVUS imaging guidewire should preferably satisfy several requirements. As in the case of existing guidewires, including those with integrated pressure sensors, the mechanical performance of the guidewire should not be significantly altered. This can enable the guidewire to be steered and torqued reliably through sharp bends in the coronary vasculature. Thus, the outside dimensions and coatings are preferably substantially similar to conventional guidewires. In addition, a minimal number of electrical cables should be utilized so that the core wire diameter (and thus, the stiffness) is not altered, particularly at the distal end. At the coiled distal end, for example, the length of the relatively rigid sensor sections should be as small as possible (~2 mm in current FFR guidewires) to maintain high flexibility.

On the imaging side, the IVUS probe should preferably provide transverse and sagittal cross-sectional views of the artery with a resolution, penetration depth, and dynamic range comparable to existing IVUS phased array systems. Additionally, this should preferably be achieved with a non-rotating guidewire to minimize the risk of injuries to the vessel walls.

To this end, embodiments of the present invention can comprise a system comprising a high frequency IVUS imaging array front-end with interfacing and high bandwidth data transmission link electronics integrated on a single silicon chip with the dimensional profile and number of electrical connections of the existing guidewires. In some embodiments, the system can also include pressure or pressure/flow sensors to maintain current FFR and flow measurement capabilities. In some embodiments, multiple pressure sensors can be used to measure flow, for example, or Doppler techniques can be used.

As shown in FIG. 2a, embodiments of the present invention can comprise a guidewire 200 with integrated one or more CMUT-on-CMOS IVUS arrays 205. The guidewire 200 can comprise a conventional coiled end 201 with an electronics compartment 202. In some embodiments, the electronics compartment 202 can comprise a window 203, slot, or other means for direct pressure and/or temperature measurement.

As shown in FIGS. 2b-2c, embodiments of the present invention can comprise an IVUS guidewire 200 utilizing single chip systems 205 replacing the conventional FFR sensor. In this structure, CMUT-on-CMOS technology can be used to fabricate a 1-D (or 1.5 D) CMUT array 210 directly on a silicon substrate 215 with low power, low noise front-end ultrasonic Tx/Rx circuitry. In some embodiments, regulated direct current (DC) power can be delivered to the guidewire electronics via one or more pairs of 220 wires added to the core-wire 225. In other embodiments, alternating current (AC) power, which can be safer in some instances, can be delivered to the guidewire electronics via one or more pairs of 220 wires added to the core-wire 225. In some embodiments, the chip 205 can be encased in an acoustically transparent material 230 to conform to, for example, the internal dimensions of the electronics compartment 202 or the external shape of the guidewire 200.

In some embodiments, wireless data transmission from the guidewire 200 can be provided directly from the distal end 200a using an on-chip ultra wideband wireless transmitter (RF-Tx). In other embodiments, data can be transferred to the handle 235 of the guidewire 200 at the proximal end 200b after transferring data from the distal end 200a through power delivery wires via, for example and not limitation, back scattered impedance modulation (also known as load shift keying (LSK)), controller area network (CAN) technology, or RF modulation. In still other embodiments, ultrasound waveform data can be transferred to the handle 235 of the guidewire 200 at the proximal end 200b after transferring data from the distal end 200a through one or more additional pairs of wires.

In some embodiments, data can be delivered from the handle 235 to a PC wirelessly via a wideband commercial-off-the-shelf (COTS) RF transceiver, such as wireless USB or WiFi, similar to the St. Jude Aeris wireless FFR system. In other embodiments, data can be delivered from the handle 235 to a PC via a wired connection such as, for example and not limitation, USB or Firewire. In still other embodiments, the handle 235 can comprise internal or external, removable memory (e.g., USB thumb drive, Flash card, etc.) to store data for retrieval at a PC, or other suitable machine.

Regardless, the data transmission link and power management electronics can be integrated on the same CMUT-on-CMOS system-on-a-chip (SoC) 205. In some embodiments, the wireless data transmitted from the guidewire 200 can be received by a small area planar ultra wideband (UWB) antenna attached to the patient's chest in the form of an adhesive patch (similar to ECG electrodes) or a wireless USB dongle on a nearby PC.

As shown in FIG. 2b, a properly scaled cross sectional view of the 0.014" guidewire 200 shows that the 1-D CMUT arrays 210 can have a lateral aperture, with its width limited by the diameter of the guidewire, of approximately 300 μm for this particular guidewire and elements as long as approximately 1 mm. These CMUT arrays 210, when operated around an approximate 40 MHz center frequency, can provide lateral resolution comparable to current 3.5F commercial 20 MHz IVUS phased array probe. The operation frequency of these CMUT arrays can be increased to improve the image resolution as well known in the art.

As shown in FIG. 2c, embodiments of the present invention can also comprise one or more ultrasonic arrays arranged in a 3-D geometry. Each CMUT array 210 has an approximately 90° field of view. As a result, in some embodiments, two pairs of thinned-down CMUT arrays 210a, 210b (i.e., CMUT arrays disposed on thinned-down silicon chips) can be positioned such that they cover approximately 360°. As shown a first pair of CMUT arrays 210a can be positioned back to back in an approximately vertical orientation, while a second pair of CMUT arrays 210b can be positioned in a substantially vertical direction. The slight difference in position of the arrays 210a, 210b along the guidewire can be easily compensated for by adding a simple time delay and "stitching" the image together to form a complete cross sectional image.

Figure 3B:
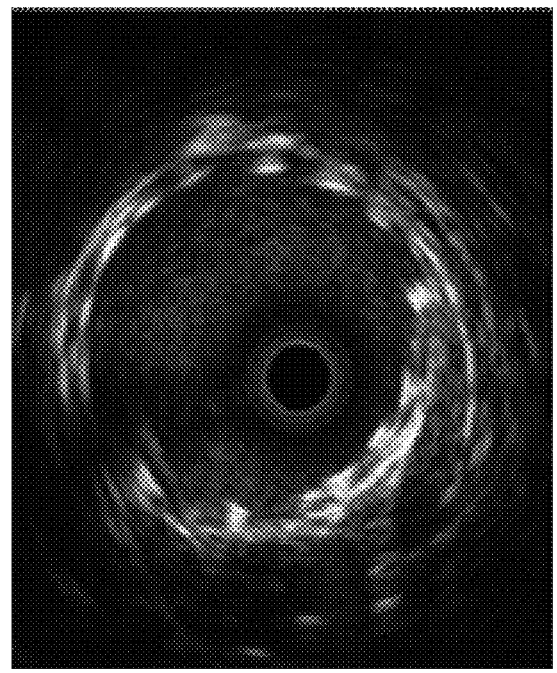
FIG. 3b depicts a 360° image created by combining images from multiple CMUT arrays, in accordance with some embodiments of the present invention.
Figure 3A:
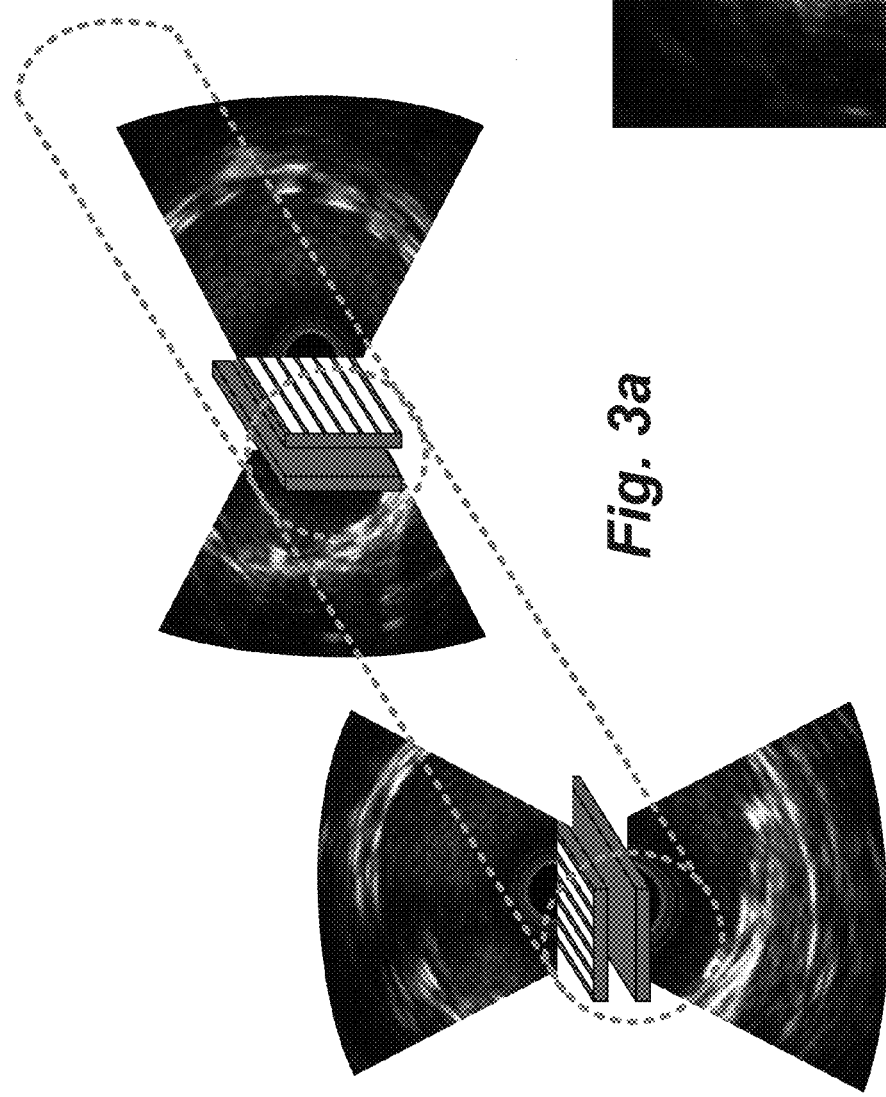
FIG. 3a depicts a perspective, side view of an IVUS sensor capsule with multiple capacitive micromachined ultrasonic transducer (CMUT) sensor arrays and their perspective images, in accordance with some embodiments of the present invention.

FIGS. 3a-3b illustrate an example of a 360° cross sectional image formation strategy from the two sets of back-to-back, thinned down CMUT-on-CMOS SoCs 210a, 210b. In some embodiments, each chip 210 can sequentially generate approximately a 90° sector image using synthetic phased array beamforming. In this configuration, the four generated images can be "stitched" together on the screen to provide the full transverse cross sectional images with a frame rate similar to the current IVUS systems.

In some embodiments, the SoC chips 210 can be placed end-to-end such that they have substantially the same geometry as the sensor section 115 of current FFR guidewires. This can also reduce and fix the distance between the image sectors to between approximately 0.5-1 mm. In this configuration, the sagittal cross sections obtained by the guidewire IVUS 200 during pull back will be substantially identical to current IVUS probes with an approximately 0.5 mm shift between certain angular sectors.

In some embodiments, as shown in FIG. 2c, an FFR sensor 245 can be integrated on a small area on one of the chips. In this configuration, a capacitive pressure sensing FFR membrane (basically a large CMUT) 225 and capacitive sensor electronics can easily be integrated into the chip 215. The membrane 225 can be made large and flexible for low frequency pressure response (i.e., as opposed to the small, stiff membranes used on the CMUTs for ultrasonic pressure response). In some embodiments the FFR sensor can be a piezoresistive sensor on the same chip as the CMUT imaging chip or it can be on a separate chip but electrically and mechanically connected to the CMUT imaging chip.

Figure 4:
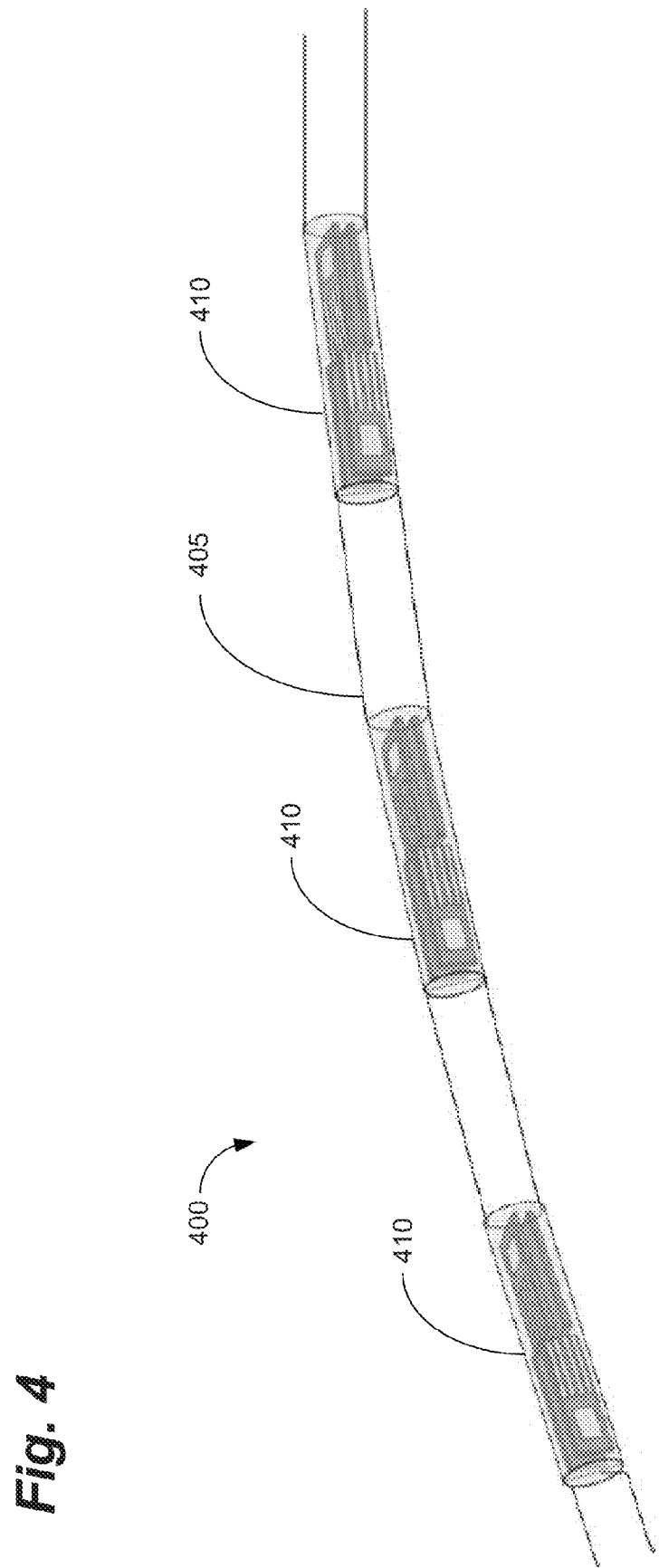
FIG. 4 depicts a guidewire with multiple CMUT arrays disposed along its length, in accordance with some embodiments of the present invention.

In some embodiments, as shown in FIG. 4, the system can be implemented with multiple sensor arrays. In this configuration, the system 400 can comprise a guidewire 405 with multiple CMUT-on-CMOS imaging arrays 410 disposed at predetermined distances along the wire 405. In this manner, imaging of a larger area can be performed without moving the guidewire 405 (or with the need for movement substantially reduced). This can enable the mapping and diagnosis of a larger area in an artery, for example, without the increased risks associated with guidewire 405 pullback. In some embodiments, the images from each array 410 can also be stitched together to create a larger 3D image of the surrounding tissue.

The inventors' prior work has shown that one can implement a CMUT-on-CMOS imaging system can provide clinical quality ultrasound images in 20 MHz where it can output RF data through 4 parallel channels with approximately 0.8 mW/ch.[2] The imaging chip comprises low noise transimpedance amplifiers (TIAs) as Rx amplifiers and 25V single transistor Tx pulsers. The total power consumption is approximately 20 mW, most of which is used by the buffers (e.g., active TIAs for 4 parallel RF channels only consume approximately 3.2 mW). Significantly, however, the area for each TIA is approximately 25 μm×55 μm, while the pulsers are even smaller in the current 0.35 μm CMOS process. As a result, in some embodiments for IVUS imager on a guidewire, with a single Tx pulser and Rx TIA active at any given time, and negligible power consumed by Tx pulsers and digital control circuits, approximately 10% of the 300 μm ×1000 μm silicon chip is utilized. In addition, on average, only about 2 mW of power will be consumed by the entire analog front end for IVUS imaging guidewire SoC.

[2] See, e.g., Gurun, "Single-chip CMUT-on-CMOS front-end system for real-time volumetric IVUS and ICE imaging", IEEE Transactions on Ultrasonics, Ferroelectrics and Frequency Control, 0885-3010, 61:2, 239 (2014) (which is incorporated herein by reference as if set forth below).

Figure 5C:
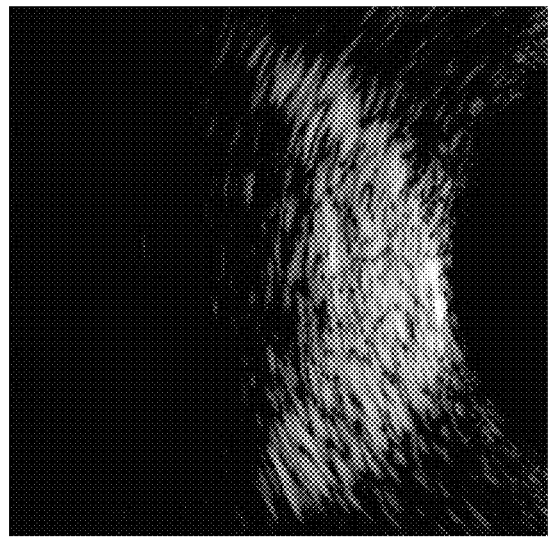
FIG. 5c depicts a cross sectional image of the chicken heart with 40 dB dynamic range, in accordance with some embodiments of the present invention.
Figure 5A:
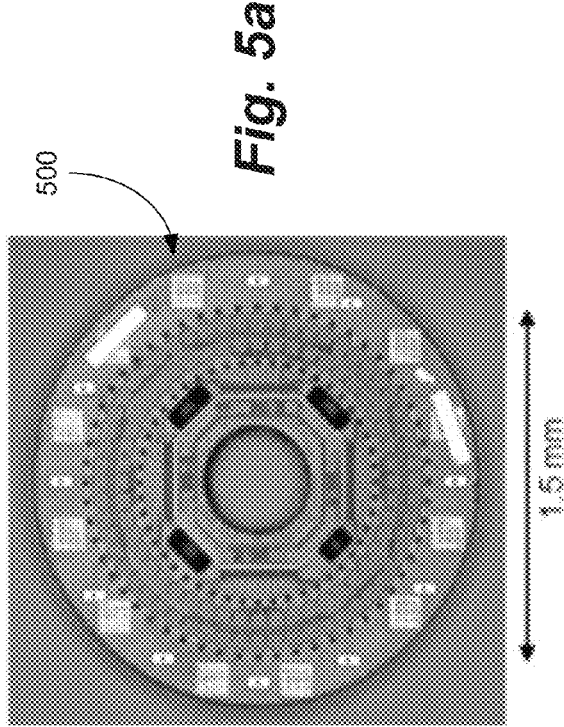
FIG. 5a depicts a donut shaped FL-IVUS chip for experimental use, in accordance with some embodiments of the present invention.
Figure 5B:
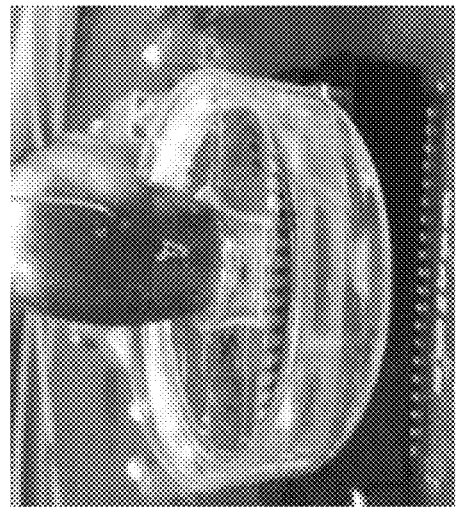
FIG. 5b depicts an experimental setup for imaging a chicken heart, in accordance with some embodiments of the present invention.

FIG. 5b depicts the experimental setup used to obtain volumetric image data from a chicken heart using the dual-ring array from the aforementioned reference. The cross sectional image (8 mm×10 mm) of the heart wall is shown in FIG. 5c with 56 dB image dynamic range using real-time data collected at 60 fr/s without averaging, showing adequate dynamic range, resolution and penetration depth provided by CMUT-on-CMOS chips for IVUS. With the larger overall array area of the 1-D array elements, one would expect to have similar or improved performance from the guidewire IVUS system, especially using the aforementioned delay schemes to implement 1.5D arrays.

Ultra-wideband Wireless Data Links and Over the Wire Power Delivery

Figure 6A:
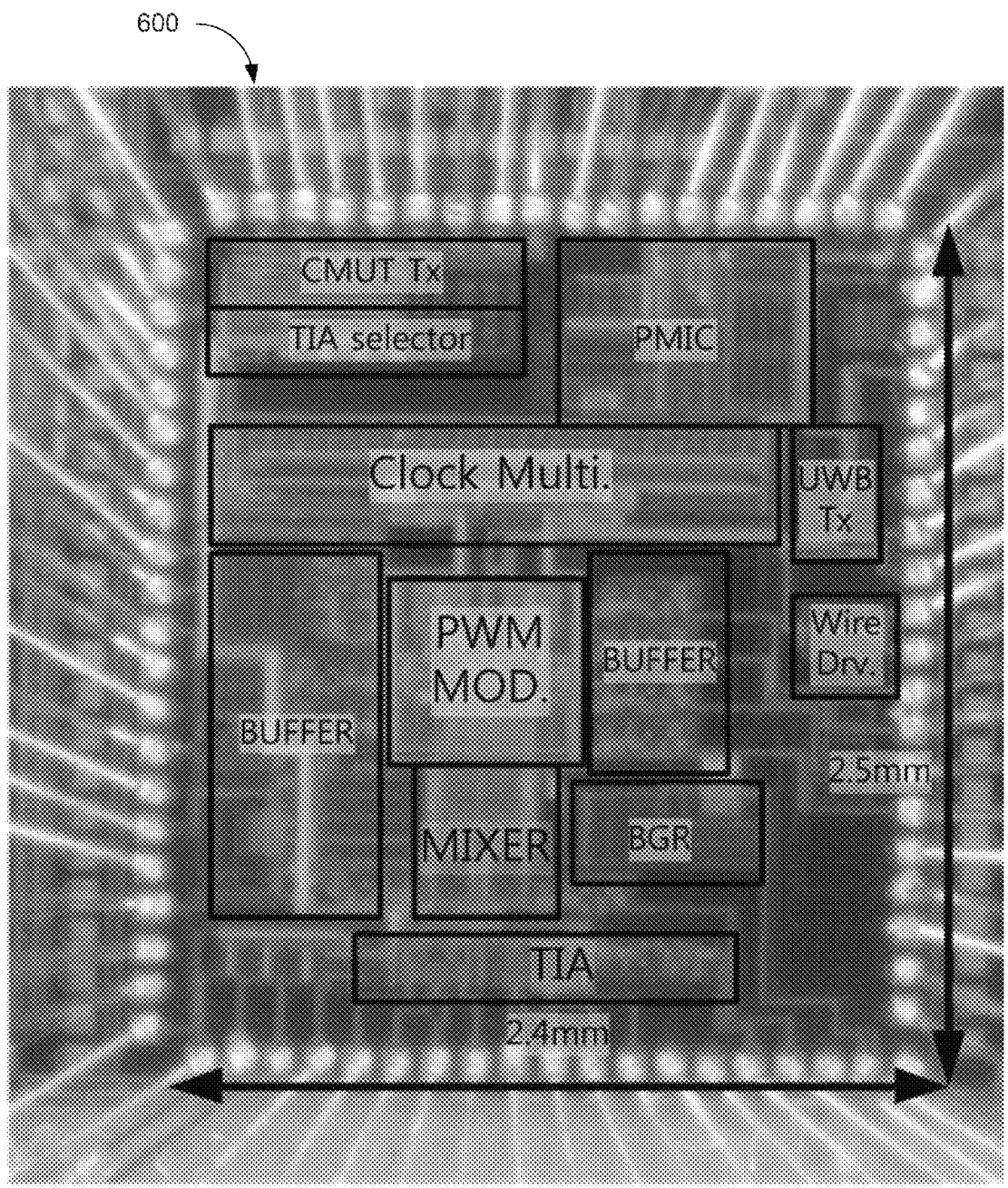
FIG. 6a depicts a WINeR-6 system on chip (SoC) with a 32 channel low-noise amplifier, 13.56 MHz inductive power management IC, and 915 MHz RF transmitter, in accordance with some embodiments of the present invention.
Figure 6B:
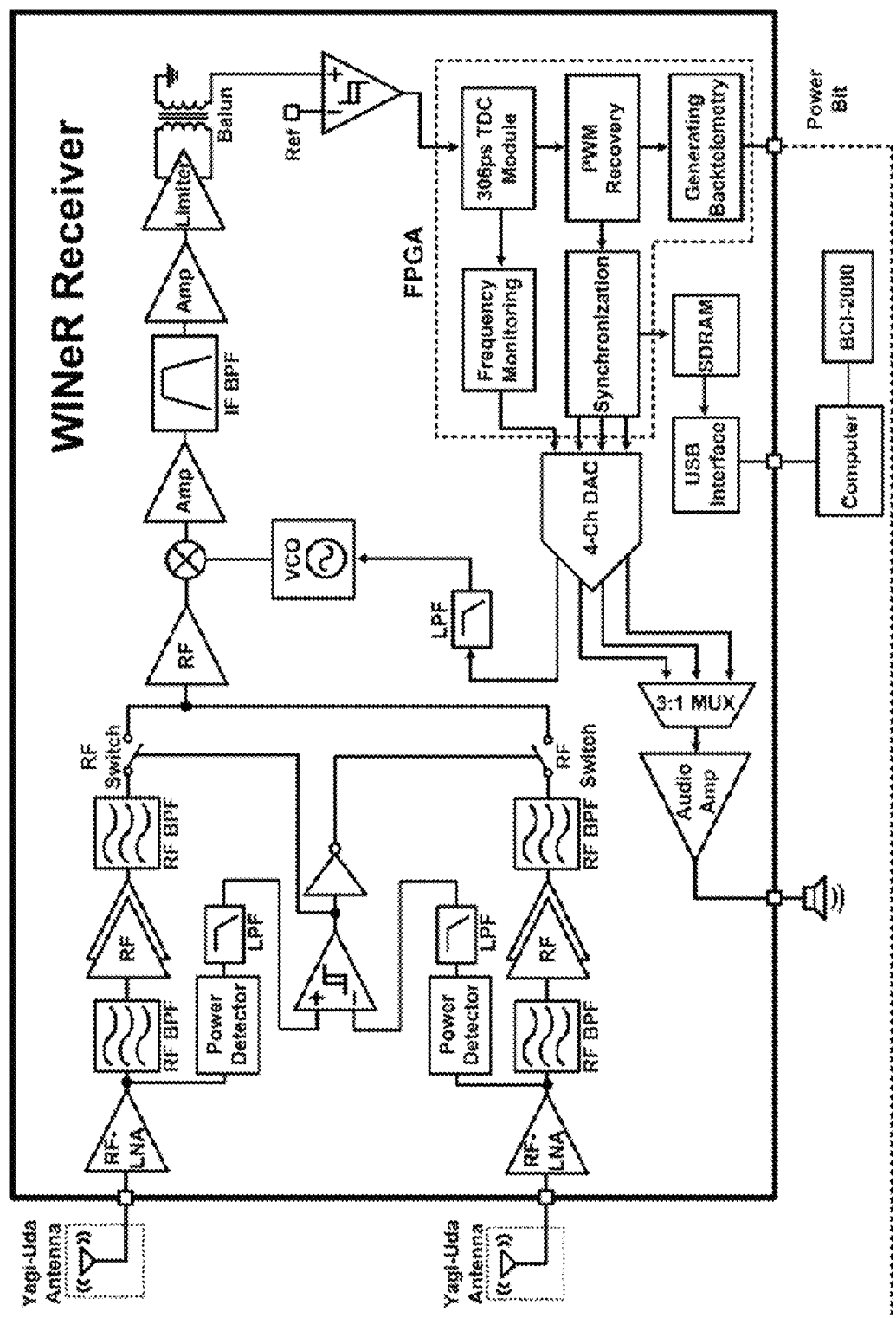
FIG. 6b depicts a block diagram of an ultra-wideband receiver circuit, in accordance with some embodiments of the present invention.
Figure 7:
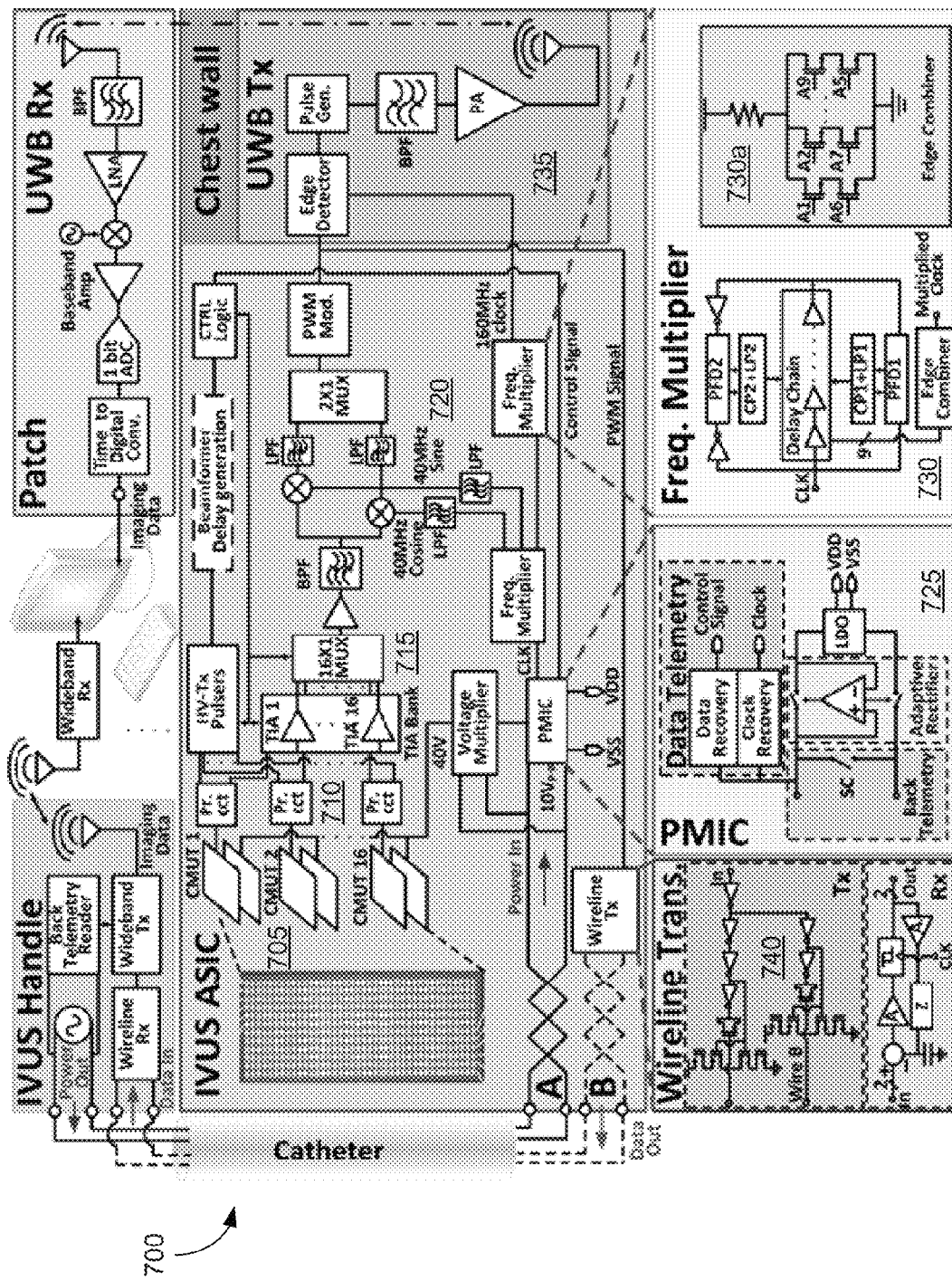
FIG. 7 is an exemplary block diagram of the CMUT-on-CMOS System-on-a-Chip on the distal end of the guidewire of FIGS. 6a-6b, in accordance with some embodiments of the present invention.

Data from the IVUS array can be transported out of the body using a number of communications protocols. One of these protocols is ultra-wideband wireless data links. FIGS. 6a-6b depict a SoC wireless transceiver 600. In some embodiments, as shown in FIG. 6a, the SoC can comprise 32 channel low-noise amplifiers (LNA), tunable bandpass filters, 13.56 MHz inductive power management IC (PMIC), and 915 MHz wideband frequency shift keying (FSK) RF transmitter on a single SoC 600. In some embodiments, as shown in the block diagram in FIG. 6b, the SoC 600 can also comprise a wideband ultra-sensitive receiver and multiple high gain antennas to acquire high throughput data and deliver it to a PC via USB, while providing sufficient coverage over a large experimental area. In this configuration, the SoC 600 consumes less than approximately 15 mW, on average. FIG. 6a depicts the first implementation of the wireless CMUT interface chip in a 0.35 um standard CMOS process, the block diagram for which is shown in FIG. 7. This chip includes the interface circuits for driving and receiving analog signals from the CMUTs (CMUT Tx), power management circuitry (PMIC), and wireless ultra wideband data transmission circuits (UWB Tx). Moreover, it has the necessary circuits to send data back from the distal to the proximal end of the catheter through the same wires as the power delivery using LS K.

In other embodiments, the system can also utilize wireless power transfer (WPT) and multi-carrier transcutaneous bidirectional data transmission methods developed with high efficiency and bandwidth. In some embodiments, relatively low frequency bands (e.g., less than 10 MHz) can be used for power, medium (e.g., approximately 25-50 MHz) can be used for forward data, and high (e.g., higher than 1 GHz) frequency can be used for back telemetry functions. Of course, other combinations and permutations could be used and are contemplated herein.

Figure 6C:
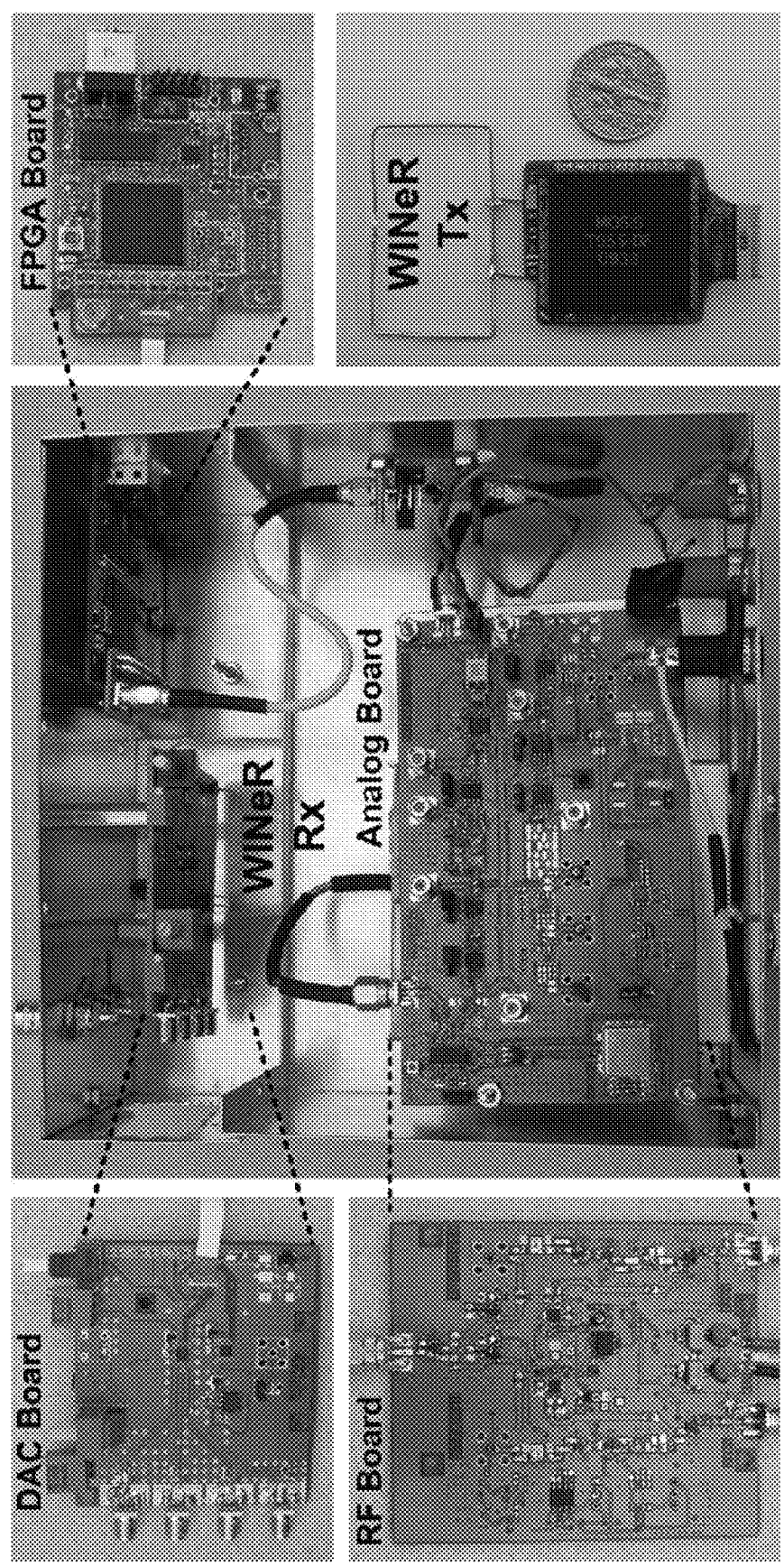
FIG. 6c depicts external circuitry for ultra-wideband data transceiver functions, in accordance with some embodiments of the present invention.

FIG. 6c depicts an exemplary embodiment of the external circuitry for transmitting and receiving data to/from the SoC shown in FIGS. 6a-6b outside the body. As shown, the external system can comprise a digital-to-analog convertor (DAC Board), a radiofrequency board (RF Board) for sending and receiving data via RF signals, a field programmable gate array board (FPGA Board), a wideband RF transmitter (WINeR Tx), a wideband RF receiver (WINeR Rx) and an analog board. Of course, other configurations could be used and are contemplated herein. For example, the FPGA board could be replaced with a custom application specific integrated circuit (ASIC).

EXAMPLE 1

An exemplary overall block diagram of a CMUT-on-CMOS based IVUS SoC 700 is shown in FIG. 7. As shown, in some embodiments, the system 700 can comprise one or more high frequency CMUT arrays 705 (designed for the imaging specifications), and front-end analog electronics including one or more of Tx/Rx protection circuits 710, amplifiers 715, and pulsers 720. In some embodiments, additional circuits can be designed for this particular application, as discussed below.

In some embodiments, for example, a unique power management IC (PMIC) 725 can efficiently convert an incoming 10 MHz AC signal from a pair of wires to high and low DC levels for use on the CMUT and CMOS electronics, respectively. The frequency of the AC signal can be selected between 0.1 to 100 MHz depending on the requirements of the CMOS circuit. In some embodiments, the 10 MHz power carrier signal can also be used to generate a 10 MHz on-chip time base, which can be further multiplied by one or more frequency multipliers 730 or divided by one or more dividers to generate higher or lower frequency clock signals for use by other blocks, respectively. In some embodiments, for example, a 40 MHz signal can be generated for the front-end down-converter 740 (to substantially limit the bandwidth of the analog ultrasound signal to 10 MHz) and 3-10 GHz can be generated for the UWB-Tx 735. In some embodiments, an edge combiner 730a, for example, can be utilized for frequency multiplication, by accurately delaying the timebase using delay-locked loops (DLL) and then mixing it with other delayed clocks. In another embodiment, an on-chip oscillator can be used to independently generate the high frequency carrier signal needed for wireless data transmission.

In other embodiments, a super heterodyne technique can be used to down-convert the analog signal and limit its bandwidth to 10 MHz before quadrature sampling and modulation. Of course, the system's RFIC-inspired architecture is frequency-scalable. As a result, higher frequency IVUS operation can be achieved by multiplying the 10 MHz timebase by N to down convert a Nx10 MHz IVUS signal to the baseband. In other words, the disclosure of specific frequencies herein is purely exemplary and other frequencies are possible and contemplated.

Since high speed analog to digital converters (ADC) tend to consume considerable power (e.g., flash ADC) and/or occupy large SoC real estate (e.g. SAR-ADC), in some embodiments, they can be replaced on the CMUT SoC with simple but high speed comparators. Comparators convert the down-converted analog samples to pulse width modulated (PWM) pulses in a process also known as amplitude-to-time conversion (ATC). The resulting PWM signal has the same benefits of digital signals (i.e. binary 0 and 1 levels) and therefore tends to be quite robust against noise and interference. The comparators can maintain at least 8-bit resolution with 10 MHz bandwidth, which is suitable for IVUS image dynamic range. Using current technology, in fact, the PWM method can be used up to approximately 200 MHz analog bandwidth.

The PWM signal can then be RF-modulated and transmitted wirelessly via an on-chip RF transmitter or ultra wideband transmitter. The RF signal propagates through tissue with some losses and is received by receiver antennas that can be attached to the surface of the skin as patches as close as possible to the distal end of the catheter. In an exemplary embodiment, these receiver antennas are wired to the front end of the external receiver, similar to FIG. 6x, which demodulates the RF signal to recover the PWM signal. The receiver then measures the duration of each recovered PWM pulse in a process also known as time-to-digital conversion (TDC). The digitized samples are then delivered to a computer or storage system via USB or Ethernet for further signal processing and generation of the ultrasound image.

Figure 8A:
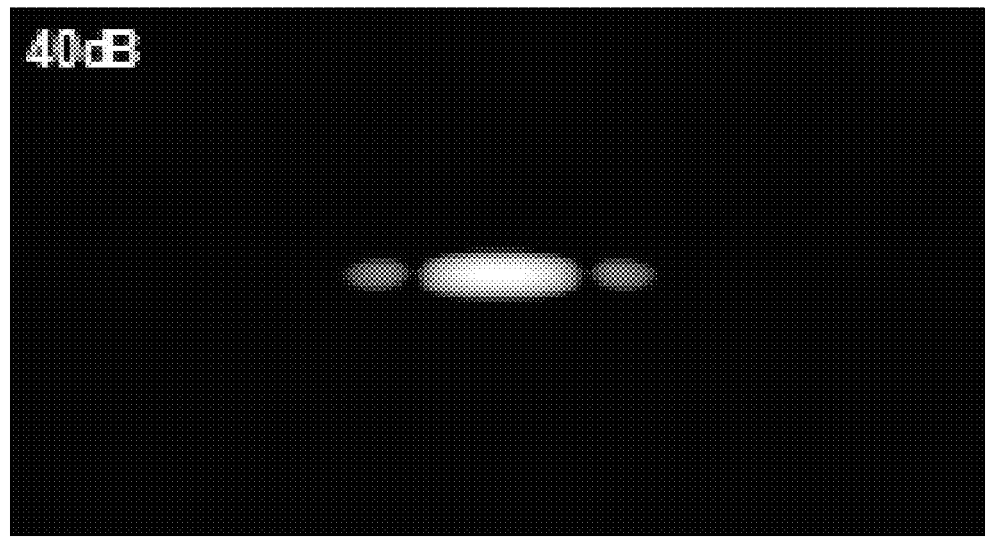
FIGS. 8a-8b depict a point spread function (PSF) for 40 MHz guidewire IVUS (4a) vs. a 20 MHz commercial IVUS (4b), in accordance with some embodiments of the present invention.
Figure 8B:
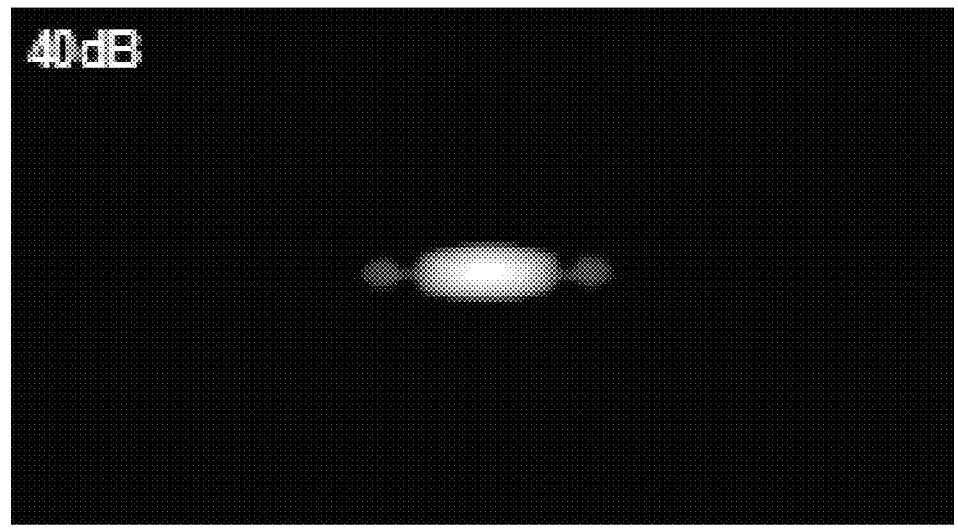
Figure 8C:
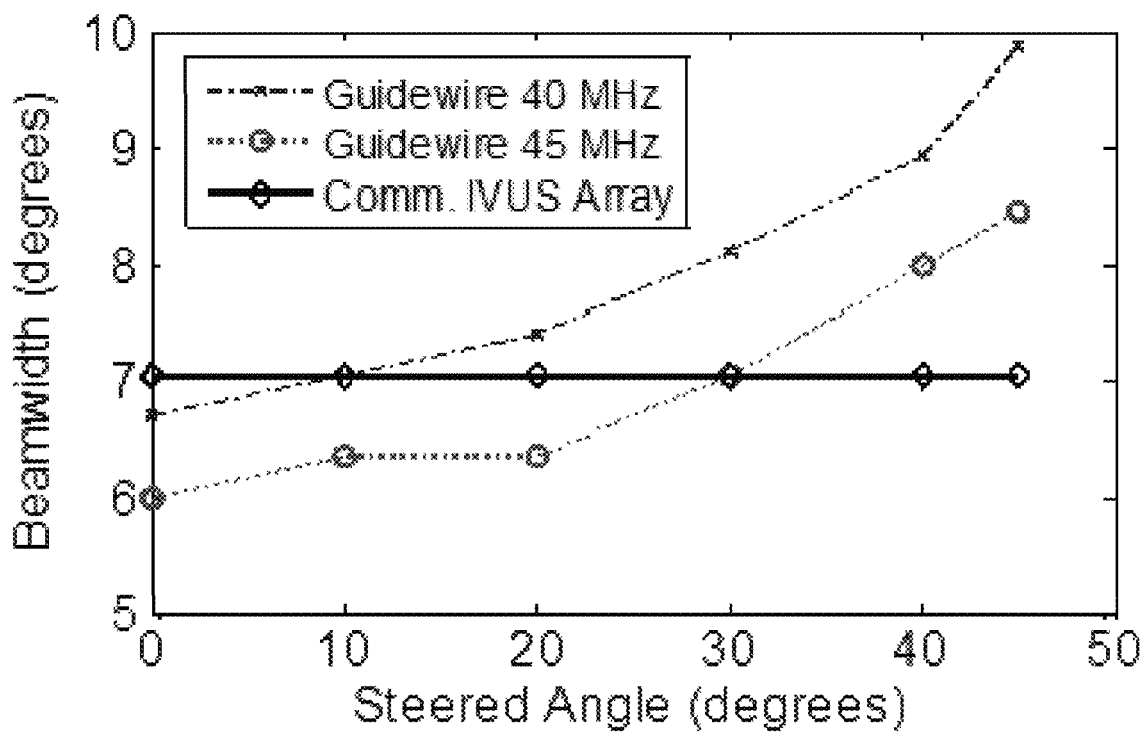
FIGS. 8c-8d depict a comparison on beamwidth vs. steering angle (8c) compared to an on axis beam (8d), in accordance with some embodiments of the present invention.
Figure 8D:
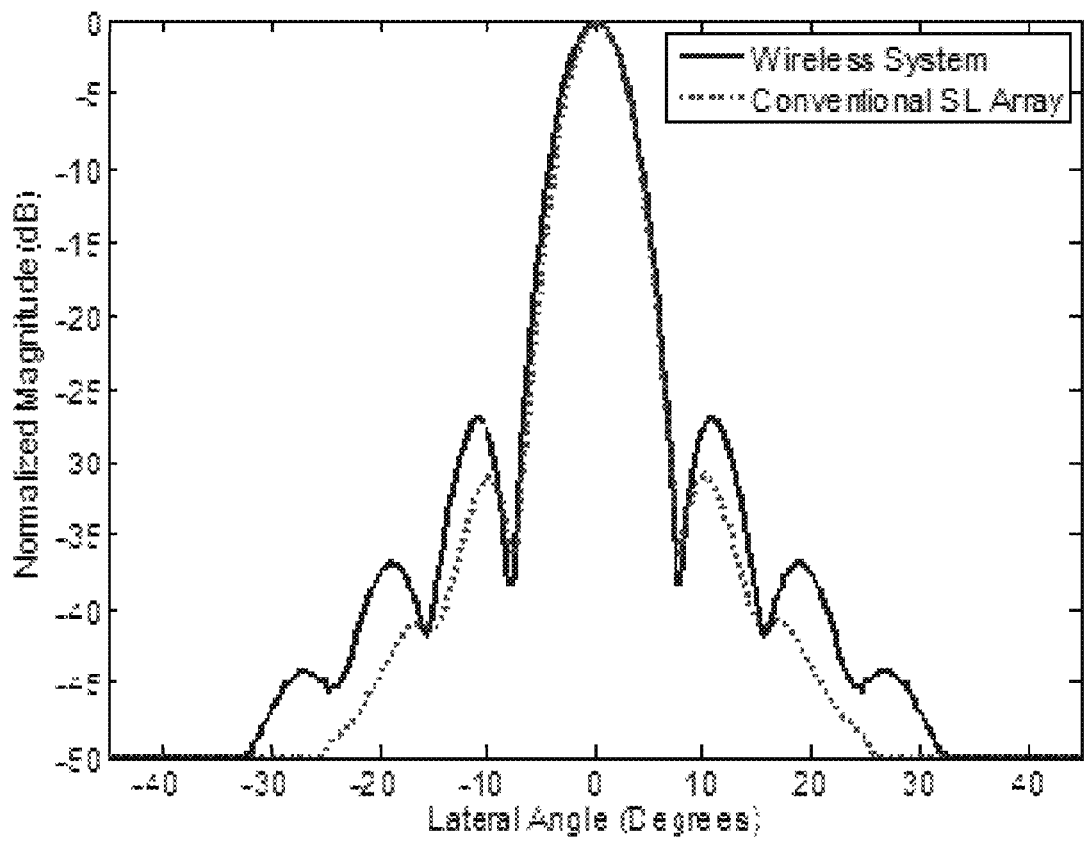

Design and Fabrication of IVUS Imaging Guidewire Arrays and Front-End Electronics In some embodiments, the guidewire IVUS system can provide similar resolution to current 3.5F 20 MHz IVUS phased array systems. Using the available 300 µm aperture 203 on the guidewire IVUS 200, a 16 element, 40-45 MHz 1-D CMUT array with 10 MHz bandwidth can be implemented with 18 µm pitch. FIGS. 8a-8d compare the simulated on axis and steered point spread function (PSF) of such an array with 3.5F commercial IVUS array with 20 MHz center frequency and 8 MHz bandwidth. FIGS. 8a-8b depict the PSF for the 40 MHz guidewire IVUS (8a) vs. 20 MHz commercial IVUS (8b). FIGS. 8c-8d compare the beamwidth and steering angle for the steered point (8c) and on axis beam pattern (8d).

As shown, the axial resolution of guidewire IVUS is better and lateral resolution is comparable over the 0-45° steering range. The number of firings for a sector image can be 136 for each chip and thus the frame rate can be the same as the current IVUS systems. Of course, more or less firings can be used for higher or lower framerates.

EXAMPLE 2

Figure 9A:
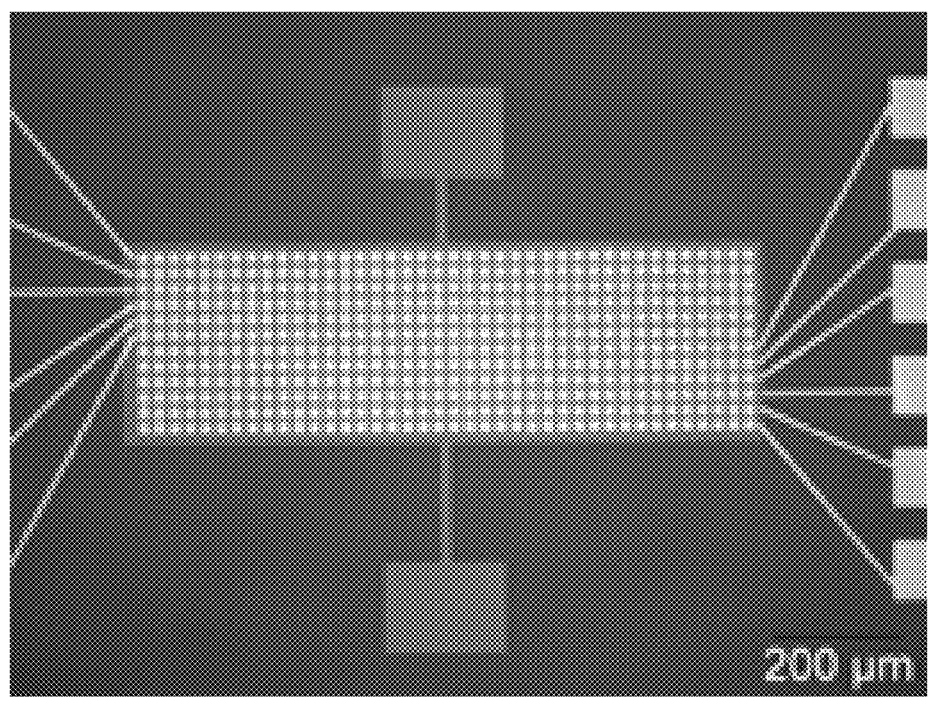
FIG. 9a depicts a micrograph of an exemplary guidewire IVUS chip, in accordance with some embodiments of the present invention.
Figure 9B:
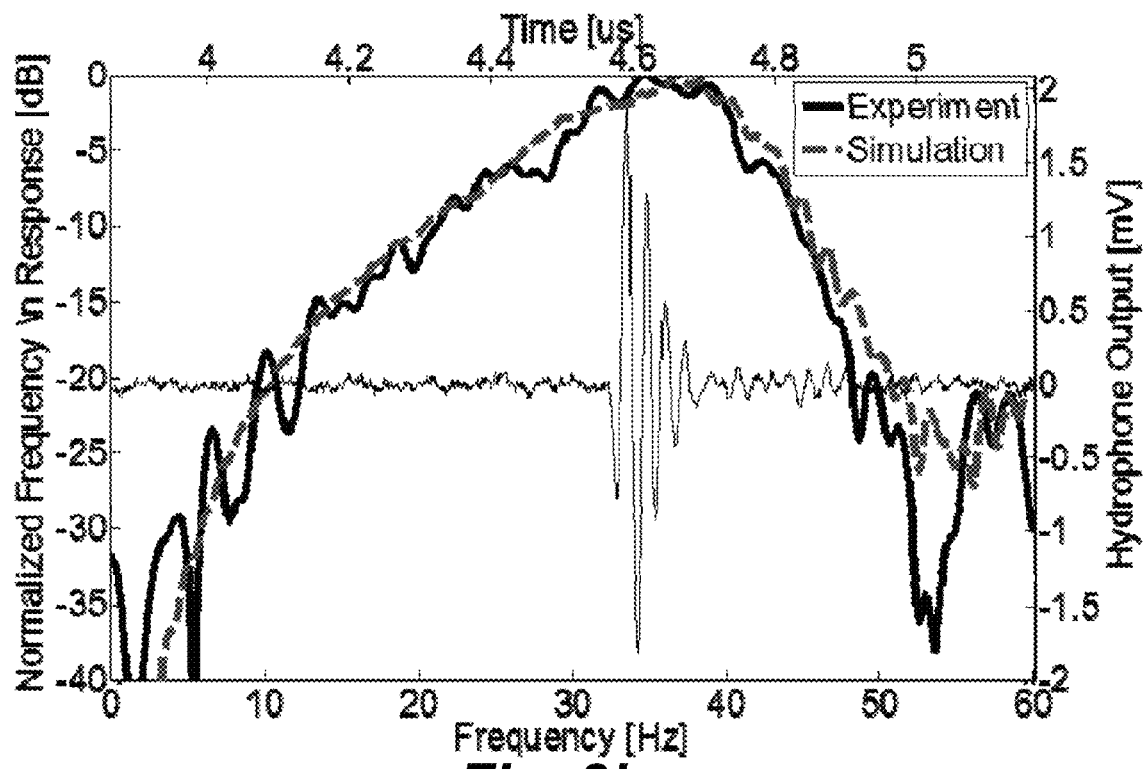
FIG. 9b is a graph of the recorded transmit pressure in time and frequency domains (0-60 MHz, compared with simulation in red), in accordance with some embodiments of the present invention.

As shown in the micrograph depicted in FIG. 9a, in some embodiments, a 12 element 38 MHz array with 20 µm square CMUT membranes and 25 µm pitch can be used. FIG. 9b depicts the frequency response and recorded transmitted pulses with appropriate frequency response. To achieve a 40V collapse voltage with 45 MHz center frequency and large Tx swing with 25V pulses, the CMUT gap thickness can be reduced to 50 nm, with 2.5 µm thick, 16 µm square PECVD nitride membranes. In other embodiments, higher frequency CMUTs can be fabricated using smaller and/or stiffer membranes to improve the overall resolution.

Broadband Data Link for IVUS Imaging Guidewire

Figure 10:
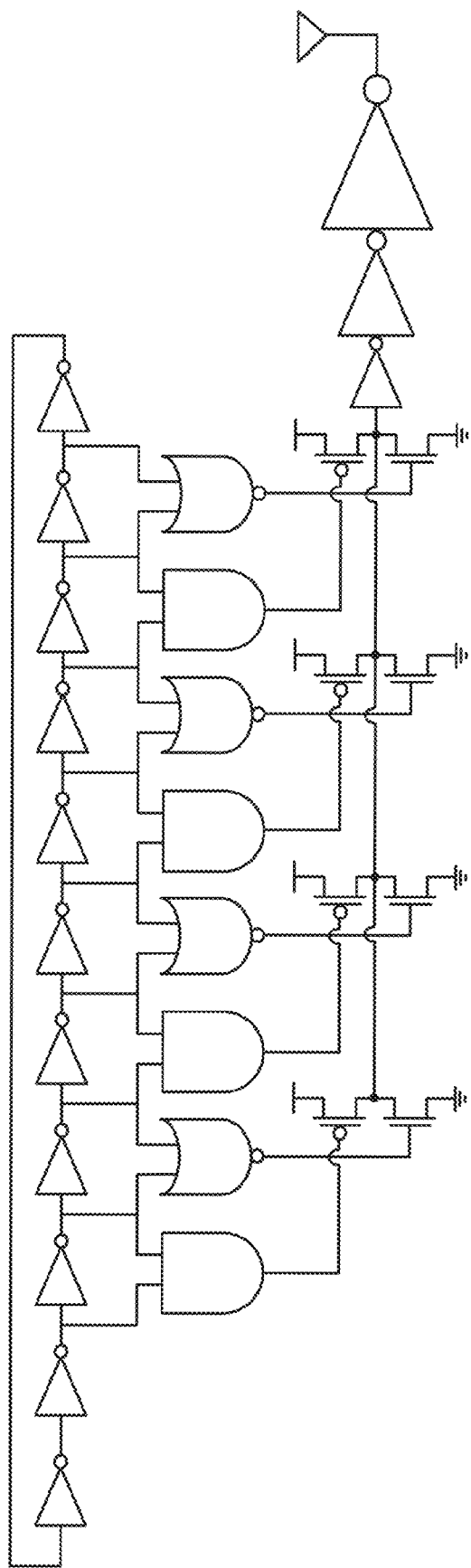
FIG. 10 depicts a sharp pulse generator in the UWB block, in accordance with some embodiments of the present invention.

Due to the volume of data required for IVUS imaging, data transfer from the electronics to the outside world can be challenging. To this end, in some embodiments, direct wireless data readout from the distal end of the guidewire can be used. In this configuration, the rising and falling edges of the PWM signal can be used in the UWB block to trigger a unipolar sharp impulse generator circuit, as shown in FIG. 10. In some embodiments, these pulses can be shaped by a bandpass filter (BPF) and transmitted after passing through a wideband RF power amplifier.

In some embodiments, the Tx antenna can be a piece of wire with tuned length that can be aligned with the guidewire. Though this is not the most efficient IR-UWB antenna available, it is useful due to the size constraints of the guidewire. The relatively small gain of this type of antenna can also be compensated for by the proximity of a patch Rx antenna on the patient's chest and the sensitivity of the external IR-UWB receiver, with an embodiment shown in FIG. 6x. If ringing on the Rx side limits the data rate, the Pulse Harmonic Modulation (PHM) concept can be used by transmitting a pair of successive IR-UWB pulses per edge of the PWM.[3] In this configuration, the first pulse can initiate an oscillation at the output of the high-Q patch antenna and the second one can end it by producing an oscillation that is 180° out of phase.

[3]See, e.g., F. Inanlou and M. Ghovanloo, "Wideband near-field data transmission using pulse harmonic modulation," IEEE Trans. on Circuits and Systems I, vol. 58, no. 1, pp. 186-195 (January 2011); F. Inanlou, M. Kiani, and M. Ghovanloo, "A 10.2 Mbps pulse harmonic modulation based transceiver for implantable medical devices," IEEE J. Solid-State Circuits, vol. 46, no. 6, pp. 1296-1306 (June 2011).

In some embodiments, received pulses from the chest antenna can be filtered, amplified, and passed through a 1bit ADC (i.e. a comparator) to recover the PWM signal. In some embodiments, such as the one shown in FIG. 6x, a time-to-digital converter (TDC) can be used to measure the width of the PWM pulses, which are proportional to the analog samples, with high timing resolution (e.g., on the order of <100 ps). The resulting digitized data can then be transferred to, for example and not limitation, a PC, mainframe, or network facility via wireless USB, WiFi, or UWB. In some embodiments, the all IR-UWB-Rx functions can be implemented on an application specific integrated circuit (ASIC). In other embodiments, it can be implemented on a custom designed discrete COTS RF component. In an exemplary embodiment, the system can comprise a ZX60-3011+Wideband LNA (Mini-circuits, Brooklyn, N.Y., which has 400 MHz-3 GHz bandwidth), an AD8348 mixer (Analog Devices, Boston, Mass.), and an AD4899-1 LNA (Analog Devices, Boston, Mass.).

In other embodiments, if the quality of the received IR-UWB pulses across the chest is not sufficient to enable at least 8 effective number of bits (ENOB) in the overall system resolution, in other embodiments, LSK can be used by applying the sharp pulses that are synchronized with the PWM edges to a fast switch across the power delivery lines. In other words, only the two available power wires are required to provide both power and broadband communication. In this configuration, small changes in impedance across the power line can be detected on the proximal end of the guidewire using, for example, a wideband current sensor and a bandpass filter that constitute a reader inside the IVUS handle. This method is similar to radio frequency identification (RFID), but can achieve considerably higher bandwidth because of the wideband hardwire connection between the LS K switch and the reader. In this embodiment, the output of the reader would be the recovered PWM signal, which can be digitized using a TDC and transmitted by a commercial wideband transmitter.

In still other embodiments, as shown in FIG. 7 with dashed lines, the system can use a second pair of wires in the IVUS guidewire. In this configuration, high speed wireline techniques can be used. The system can use, for example, a capacitive transmitter, which are often used in local area networks (LAN), that reduces the RC delay to achieve data rates in excess of 1 Gb/s, well in excess of the approximately 200 Mb/s needed in this application. Since capacitive transmitter generates a low-swing signal, a differential interconnection is preferable to minimize crosstalk. In some embodiments, in the IVUS handle, a continuous time decision feedback equalization technique, which senses the received input and compares it with the previous input to decide its state, can be used.

In still other embodiments, system can use a second pair of wires or another wire in the IVUS guidewire to send the received ultrasound RF data from the CMUT array elements directly to the back end electronics and handle after on-chip amplification and multiplexing similar to described in an aforementioned system. See, Footnote 2, above. In this case, there is no need to modify the frequency content of the signal, i.e. limit the bandwidth. The broadband RF signal, which can contain frequencies up to 100 MHz, can be sent out directly on the wires and then digitized in the back end for image processing.

In terms of power consumption, the entire SoC consumes less than 150 mW for the wireless embodiment, and 100 mW in the case of hardwired data transmission. In either case, this amount of power is well within the feasible range for the AC-powered PMIC and does not represent any risk of temperature rise beyond safe limits for acute procedures.

Embodiments of the present invention, therefore, combine recent advances in guidewire sensor technology in terms of physical implementation. Electrical connections provided on the guidewire can utilize AC power supply for increased safety and low phase-noise timebase for wireless/broadband data links. CMUT-on-CMOS technology is exploited for electronics integration and in a novel physical arrangement to enable full cross sectional IVUS images with adequate resolution. Broadband, ultra-compact, short-range, and low power wireless or two- or four-wire LSK data links, or two wire direct ultrasound RF data transmitters after receiver channel multiplexing can be integrated on the same chip and used to minimize the number of cables to as few as two, retaining the mechanical performance of the guidewire.

In some embodiments, current FFR guidewire geometry is unchanged by simply changing the rigid FFR capsule with the new imager disclosed herein. In some embodiments, the platform can include future combination devices such as IVUS-FFR guidewires. In some embodiments, several imaging capsules can be included along the guidewire to collect volumetric images without pullback.

In still other embodiments, multiple stacked IC chips under the CMUT or CMUT-on-CMOS chip can be used to accommodate the required electronics under the same small area as the CMUT array and FFR sensor. The CMUT arrays can be driven with appropriate phasing so that the 4 sectors are sampled from approximately the same transverse cross section of the artery. In addition, the chips can be curved or tilted to improve the array aperture size and physically align the transmit-receive beams so that the 4 sectors comprise approximately the same transverse cross section of the artery.

While several possible embodiments are disclosed above, embodiments of the present invention are not so limited. For instance, while several possible components, chip layouts, and logic schemes have been disclosed, other suitable components, materials, and layouts could be selected without departing from the spirit of the invention. In addition, the location and configuration used for various features of embodiments of the present invention can be varied according to a particular application or imaging need that requires a slight variation due to, for example, the materials used and/or space or power constraints. Such changes are intended to be embraced within the scope of the invention.

The specific configurations, choice of materials, and the size and shape of various elements can be varied according to particular design specifications or constraints requiring a device, system, or method constructed according to the principles of the invention. Such changes are intended to be embraced within the scope of the invention. The presently disclosed embodiments, therefore, are considered in all respects to be illustrative and not restrictive. The scope of the invention is indicated by the appended claims, rather than the foregoing description, and all changes that come within the meaning and range of equivalents thereof are intended to be embraced therein.

What is claimed is:

1. A system comprising:
   an intravascular ultrasound imaging probe structurally integrated with an intravascular guidewire, the intravascular ultrasound imaging probe comprising:
   a first silicon chip;
   one or more CMUT imaging arrays, wherein the one or more CMUT imaging arrays are disposed on the intravascular guidewire; and
   one or more CMOS electronic devices disposed on the first silicon chip, the first silicon chip disposed on the intravascular guidewire and electrically connected to the one or more CMUT imaging arrays, wherein at least one of the plurality of CMOS electronic devices is configured to multiplex a plurality of channels received from one or more of the CMUT imaging arrays.

2. The system of claim 1, wherein:
   the one or more CMOS electronic devices are disposed on a second silicon chip; and
   the second silicon chip is electrically connected to the first silicon chip.

3. The system of claim 1, wherein the one or more CMUT imaging arrays comprise a first substrate, and wherein the first substrate comprises one or more fractional flow reserve (FFR) sensors.

4. The system of claim 1, wherein the one or more CMUT imaging arrays comprise a first substrate, and wherein the first substrate comprises one or more flow sensors.

5. The system of claim 1, further comprising:
   a first wire providing a ground to the first silicon chip;
   a second wire providing AC power to the first silicon chip; and
   a third wire carrying RF communications from the first silicon chip.

6. The system of claim 1, further comprising:
a first CMUT imaging array disposed on a first side of a first silicon chip;
a second CMUT imaging array disposed on a first side of a second silicon chip;
a third CMUT imaging array disposed on a first side of a third silicon chip;
a fourth CMUT imaging array disposed on a first side of a fourth silicon chip;
wherein the first side of the first silicon chip is disposed approximately 180° from the first side of the second silicon chip;
wherein the first side of the first silicon chip is disposed approximately 90° from the first side of the third silicon chip;
wherein the first side of the third silicon chip is disposed approximately 180° from the first side of the fourth silicon chip.

7. The system of claim 1, where in the diameter of the intravascular ultrasound imaging probe is less than approximately 0.014".

8. The system of claim 1, wherein the one or more CMUT imaging arrays comprise a phased array.

9. The system of claim 1, wherein the imaging array is configured to image at least a 45 degree section of an intravascular portion.

10. The system of claim 1, wherein the one or more CMUT imaging arrays and at least one of the one or more CMOS electronic devices are disposed on the first silicon chip.

11. The system of claim 1, wherein the one or more CMUT imaging arrays are disposed on a first substrate and wherein at least one of the one or more CMOS electronic devices are disposed on the first silicon chip, and the first substrate and the first silicon chip are mechanically and electrically by stacking.

12. A system comprising:
an intravascular ultrasound imaging probe structurally integrated with an intravascular guidewire, the guidewire having first diameter and comprising:
a proximal end;
a distal end; and
a core wire;
the intravascular ultrasound imaging probe comprising:
a first electronics compartment, with a second diameter, disposed proximate the distal end of the guidewire and comprising a window;
a first silicon chip;
one or more CMUT imaging arrays, wherein the one or more CMUT imaging arrays are disposed on the intravascular guidewire; and
one or more CMOS electronic devices disposed on the first silicon chip, the first silicon chip disposed on the intravascular guidewire and electrically connected to the one or more CMUT imaging arrays, wherein at least one of the plurality of CMOS electronic devices is configured to multiplex a plurality of channels received from one or more of the CMUT imaging arrays.

13. The system of claim 12, wherein the first diameter and the second diameter are less than or equal to approximately 0.014".

14. The system of claim 12, wherein:
the one or more CMOS electronic devices are disposed on a second silicon chip; and
the second silicon chip is electrically connected to the first silicon chip.

15. The system of claim 12, further comprising one or more flow sensors, wherein at least one of the one or more CMUT imaging arrays comprise a first substrate, and wherein one or more flow sensors are disposed on the first substrate.

16. The system of Claim 12, further comprising one or more fractional flow reserve (FFR) sensors, wherein at least one of the one or more CMUT imaging arrays comprise a first substrate, and wherein the one or more fractional flow reserve (FFR) sensors are disposed on the first substrate.

17. The system of claim 12, further comprising:
a wireless transmitter disposed on the first silicon chip for transmitting data, wherein the wireless transmitter comprises an ultra-wideband (UWB) wireless transmitter; and
an external antenna for receiving the data.

18. The system of claim 17, wherein the external antenna comprises a high-gain patch antenna disposed in close proximity to the wireless transmitter.

19. The system of claim 12, further comprising:
a first CMUT imaging array disposed on a first side of a first silicon chip;
a second CMUT imaging array disposed on a first side of a second silicon chip;
a third CMUT imaging array disposed on a first side of a third silicon chip;
a fourth CMUT imaging array disposed on a first side of a fourth silicon chip;
wherein the first side of the first silicon chip is disposed approximately 180° from the first side of the second silicon chip;
wherein the first side of the first silicon chip is disposed approximately 90° from the first side of the third silicon chip;
wherein the first side of the third silicon chip is disposed approximately 180° from the first side of the fourth silicon chip.

20. The system of claim 12, wherein the one or more CMUT imaging arrays comprise one-dimensional (1D) imaging arrays.

21. The system of claim 12, wherein the one or more CMUT imaging arrays comprise one and a half dimensional (1.5D) imaging arrays.

22. A system for intravascular imaging comprising:
an intravascular ultrasound imaging probe structurally integrated with a guidewire, the guidewire having first diameter and comprising:
a proximal end;
a distal end; and
a core wire;
the intravascular ultrasound imaging probe comprising:
a plurality of electronics compartments, each with a second diameter, disposed proximate the distal end of the guidewire each comprising a window;
a plurality of CMUT imaging arrays disposed on a plurality of silicon chips;
a plurality of CMOS electronic devices disposed on the guidewire and electrically connected to the plurality of CMUT imaging arrays;
wherein at least one of the plurality of CMUT imaging arrays and at least one of the plurality of CMOS electronic devices are disposed in each of the plurality of electronics compartments; and
wherein at least one of the plurality of CMOS electronic devices is configured to multiplex a plurality of channels received from one or more of the plurality of CMUT imaging arrays.

* * * * *

UNITED STATES PATENT AND TRADEMARK OFFICE
CERTIFICATE OF CORRECTION

| | | |
|---|---|---|
| PATENT NO. | : 9,259,206 B2 | Page 1 of 1 |
| APPLICATION NO. | : 14/185728 | |
| DATED | : February 16, 2016 | |
| INVENTOR(S) | : F. Levent Degertekin and Maysam Ghovanloo | |

It is certified that error appears in the above-identified patent and that said Letters Patent is hereby corrected as shown below:

In the Claims

Column 15, line 34 should have the word --connected-- inserted between "electrically" and "by" such that lines 34 and 35 read:

--the first silicon chip are mechanically and electrically connected by stacking.--

Signed and Sealed this
Thirty-first Day of May, 2016

Michelle K. Lee
*Director of the United States Patent and Trademark Office*